US009016274B1

(12) United States Patent
White

(10) Patent No.: US 9,016,274 B1
(45) Date of Patent: Apr. 28, 2015

(54) DEVICES FOR VAPORIZING AND DELIVERING AN AEROSOL AGENT

(71) Applicant: Jackie L. White, Pfafftown, NC (US)

(72) Inventor: Jackie L. White, Pfafftown, NC (US)

( * ) Notice: Subject to any disclaimer, the term of this patent is extended or adjusted under 35 U.S.C. 154(b) by 0 days.

(21) Appl. No.: 14/053,335

(22) Filed: Oct. 14, 2013

(51) Int. Cl.
*A61M 15/06* (2006.01)
*A61M 16/00* (2006.01)
*B05D 7/14* (2006.01)
*F23D 14/00* (2006.01)
*A61M 15/00* (2006.01)
*A24F 47/00* (2006.01)

(52) U.S. Cl.
CPC .............. *A61M 15/00* (2013.01); *A24F 47/008* (2013.01)

(58) Field of Classification Search
CPC ... A24F 47/002; A24F 47/004; A24F 47/008; A61M 15/06; A61M 11/001; A61M 11/041; A61M 2205/8268
USPC ............. 128/202.21, 202.27, 203.12, 203.15, 128/203.23, 203.26, 203.27, 204.13; 131/270–273
See application file for complete search history.

(56) References Cited

U.S. PATENT DOCUMENTS

| | | | |
|---|---|---|---|
| 4,714,082 A | 12/1987 | Banerjee et al. | |
| 4,756,318 A | 7/1988 | Clearman et al. | |
| 4,771,795 A | 9/1988 | White et al. | |
| 4,819,665 A | 4/1989 | Roberts et al. | |
| 5,020,548 A * | 6/1991 | Farrier et al. | 131/194 |
| 5,144,962 A * | 9/1992 | Counts et al. | 131/194 |
| 5,388,572 A | 2/1995 | Mulhauser et al. | |
| 5,388,573 A | 2/1995 | Mulhauser et al. | |
| 5,388,574 A | 2/1995 | Ingebrethsen | |
| 5,460,173 A | 10/1995 | Mulhauser et al. | |
| 5,553,607 A | 9/1996 | Chiu et al. | |
| 5,649,554 A * | 7/1997 | Sprinkel et al. | 131/329 |
| 6,164,287 A | 12/2000 | White | |
| 6,761,164 B2 * | 7/2004 | Amirpour et al. | 128/203.26 |
| 6,990,978 B2 * | 1/2006 | Shayan | 128/203.27 |
| 7,090,830 B2 | 8/2006 | Hale et al. | |
| 7,143,766 B2 * | 12/2006 | Schuster et al. | 128/203.26 |

(Continued)

FOREIGN PATENT DOCUMENTS

DE 19854008 A1 5/2000
WO WO-2008/060558 A2 5/2008

OTHER PUBLICATIONS

The BOPP Group; BOPP Metal Fiber Cloth (product specifications and properties); 2002.

*Primary Examiner* — Tan-Uyen (Jackie) T Ho
*Assistant Examiner* — Mark K Han
(74) *Attorney, Agent, or Firm* — Christopher C. Dremann

(57) ABSTRACT

A device for vaporizing and delivering an aerosol agent includes a heat generator, a heat conductor in fluid (airflow) communication with the heat generator, and a substrate holder in heat conducting relation with the heat conductor. The heat generator is a handheld, portable torch and the heat conductor defines an annular heat conducting chamber surrounding a substrate disposed within the substrate holder that supports the aerosol agent and an aerosol forming agent. Another device is a handheld, battery-powered heat generator including a heating element in heat conducting relation with a substrate holder. The heating element is a nichrome heating coil wound about the substrate disposed within the substrate holder and electrically coupled to the battery. Another device further includes an auxiliary heat generator having an auxiliary heating element formed by a finely woven wire mesh positioned adjacent the substrate and electrically coupled to the battery.

24 Claims, 13 Drawing Sheets

(56) References Cited

U.S. PATENT DOCUMENTS 7,434,584 B2 * 10/2008 Steinberg .................. 131/194
8,251,060 B2    8/2012 White et al.
8,291,918 B2 * 10/2012 Magnon ..................... 131/271
2004/0099269 A1    5/2004 Hale et al.
2007/0062526 A1    3/2007 Schuster et al.
2013/0228170 A1 * 9/2013 Alper .................. 128/202.21

* cited by examiner

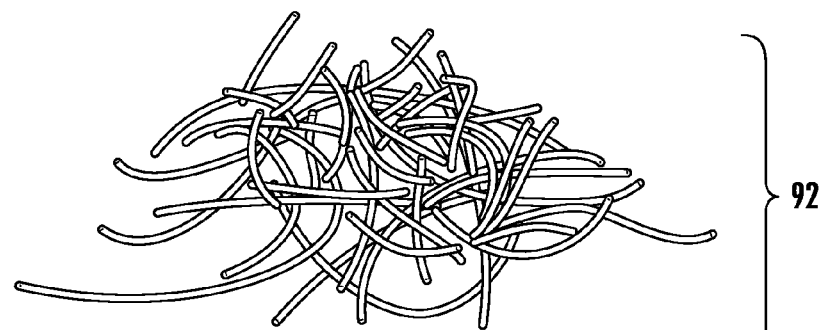
FIG. 14A
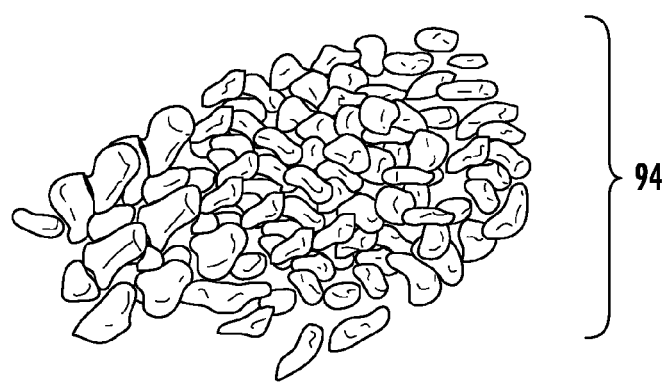
FIG. 14B
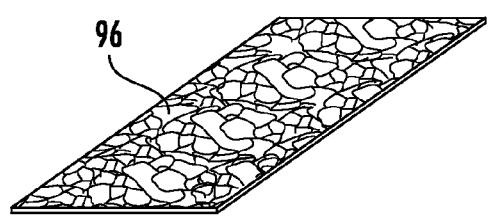 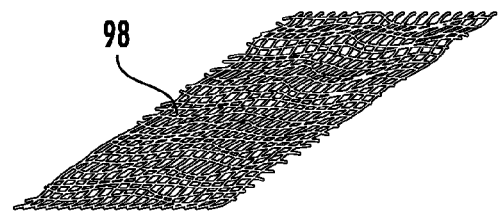
FIG. 14C    FIG. 14D

DEVICES FOR VAPORIZING AND DELIVERING AN AEROSOL AGENT

FIELD OF THE INVENTION

The present invention relates generally to devices for vaporizing and delivering an aerosol agent. In exemplary embodiments, the invention is a handheld, portable device for vaporizing and delivering an aerosol agent, for example a therapeutic drug in the form of an aerosol to a patient, or nicotine in the form of an aerosol to a smoker.

BACKGROUND OF THE INVENTION

Therapeutic agents, and in particular drugs, are commonly delivered to a patient, via a pill, capsule, tablet or the like that is ingested orally and absorbed into the bloodstream. A therapeutic agent may also be introduced directly into the bloodstream via an intravenous solution. Therapeutic agents that are ingested orally and absorbed require a longer period of time before the effects of the agent are realized by the patient. Furthermore, agents delivered to a patient via a pill, capsule, tablet or the like suffer from a loss of therapeutic effect due to hepatic metabolism. Intravenous drug delivery, however, is generally inconvenient for a patient that is not resident in a health care facility and can be painful under certain circumstances. Delivery of a therapeutic agent in the form of an aerosol by inhalation overcomes the disadvantages of both delivery methods, but has yet to gain widespread acceptance and use. One possible reason for the limited role of inhalation drug delivery despite its increased efficacy, convenience and painless administration is the lack of a suitable device for portable, reliable, repeatable and simplistic vaporization and delivery of a variety of different drugs in an aerosol form. Existing devices for vaporizing and delivering a therapeutic agent in the form of an aerosol are suitable for use with only a limited class of therapeutic drugs, such as drugs for the treatment of asthma. In addition, none of the existing aerosol agent delivery devices are sufficiently portable, reliable, repeatable and easy to use.

The adverse health risks associated with smoking cigarettes have been recognized for decades. Accordingly, approximately seventy percent (70%) of smokers today desire to reduce the amount of cigarettes they smoke, or want to quit altogether. Despite the known risks, only an estimated six percent (6%) of smokers are able to quit smoking entirely. The low rate of success is believed to be due to the highly addictive nature of nicotine present in conventional cigarettes. Nicotine gum and nicotine patches for the delivery of nicotine without the harmful by products of combustion have been available for years. Nicotine gum and nicotine patches, however, have proven to be largely unsuccessful smoking cessation devices due to their failure to satisfy the smoker's hand-to-mouth and inhalation urges. In the past few years, nicotine delivery devices in the form of combustion-free electronic cigarettes, commonly referred to as "smokeless cigarettes," "e-cigarettes" or "e-cigs," have been developed and introduced to the consuming public.

Popular brands of e-cigarettes include BLU ECIGS® offered by Lorillard Technologies, Inc. of Greensboro, N.C., VUSE® offered by Reynolds Innovations, Inc. of Winston-Salem, N.C., MARK 10™ offered by Phillip Morris, Inc. of Richmond, Va., and NJOY® offered by NJOY, Inc. of Scottsdale, Ariz. Each of the aforementioned commercially available e-cigarettes replicate the hand-to-mouth and inhalation experiences of a combustion cigarette desired by smokers. At the same time, they satisfy a smoker's craving for the addictive nicotine without exposing the smoker to the carcinogenic by-products (e.g. tar) produced by the combustion of tobacco, as well as by-standers to second-hand smoke. As a result, e-cigarettes are credited with providing a healthier nicotine delivery option to smokers and a healthy environment to by-standers subjected to second-hand smoke by significantly reducing, and potentially eliminating, the harmful effects of the carcinogens present in the smoke that would otherwise be produced and dispersed by lighting and smoking a traditional combustion cigarette.

Traditional combustion cigarettes are made of a combustible material that is ignited with a flame to cause tobacco to burn. The burning tobacco releases smoke containing nicotine that is inhaled by the smoker to deliver the nicotine to the lungs. In contrast, e-cigarettes heat a liquid, referred to as "e-liquid," containing nicotine, and in some instances flavoring, to convert the liquid into a vapor that is inhaled by the smoker to deliver the nicotine to the lungs. E-cigarettes generally include a battery, an atomizer and a hollow, re-fillable cartridge that contains the liquid nicotine. Due to the frequency required to re-fill the cartridge, an advanced type of e-cigarette has been developed that combines the atomizer and the cartridge into a single "cartomizer" connected to the battery. Cartomizers allow for a greater length of time between e-liquid re-fills. The vaporization process is initiated by the smoker inhaling on the cartridge or cartomizer, or alternatively, by the smoker depressing a manual switch that activates the atomizer or cartomizer. The atomizer heats the e-liquid and converts the liquid into a nicotine vapor in the form of an aerosol. The nicotine vapor is inhaled through a mouthpiece provided on the tip of the cartridge or cartomizer to deliver the nicotine to the lungs of the smoker. The smoker then exhales the residual vapor in the form of cigarette smoke without any combustion by-products.

Despite the reduced health risks, there remain certain disadvantages with the current e-cigarettes. In particular, the e-liquid contained within the cartridge or cartomizer typically contain a solution of propylene glycol, vegetable glycerin (VG), and/or polyethylene glycol 400 (PEG400) mixed with concentrated flavors and a highly variable concentration of nicotine. However, the liquid solutions of certain e-cigarettes still have been found to contain known cancer-causing agents, referred to as tobacco-specific nitrosamines (TSNAs), as well as tobacco-specific impurities, such as anabasine, myosmine, and β-nicotine. In fact, in a recent study the Food and Drug Administration (FDA) detected diethylene glycol, a poisonous and hygroscopic liquid commonly used in anti-freeze solutions, in the e-liquid of one brand of e-cigarette, and measurable levels of nicotine in e-liquid cartridges that claimed to be nicotine-free. These findings are particularly disturbing since the cartridges and cartomizers of e-cigarettes are inherently susceptible to leakage and/or breakage owing to their small size and relative fragility. As a result, the danger exists that a cartridge or cartomizer could leak or break and cause a user to directly inhale a harmful dosage of the liquid solution or a full nicotine delivery without vaporization. It is also possible for a leaking e-liquid to damage the electronics and/or corrode the battery of the electronic nicotine delivery device. Furthermore, the majority of e-cigarettes utilize a rechargeable lithium battery that can potentially explode if the smoking device is mistakenly exposed to the flame from a match, lighter, torch or the like.

Accordingly, an improved device that is both effective, convenient and easy to use is needed for vaporizing and delivering an aerosol agent, for example a therapeutic drug in the form of an aerosol to a patient, or nicotine in the form of an aerosol to a smoker. Such a device must be capable of vaporizing and delivering a wide range of aerosol agents in a portable, reliable, repeatable and easy to use manner. As used herein, the term "aerosol" is intended to include vapors, gases, fine particles, and the like, both visible and invisible, generated by a heat source acting upon a means for forming an aerosol in a manner consistent with the present invention. As so defined, the term "aerosol" specifically includes any pharmacologically or physiologically active agents, and any desired additives, such as an aerosol forming agent, irrespective of whether they produce a visible aerosol. As used herein, the term "in heat conducting relation" is intended to mean a physical arrangement of two or more components whereby heat is transferred by conduction or convection from a heat generating source (e.g., a heating element) to a thermally conductive component (e.g., a heat conductor or a substrate) substantially throughout the heat generating period of the heat source. A heat conducting relation can be achieved by locating the components in fluid communication, direct physical contact or in close proximity to one another during operation of the heat source.

BRIEF SUMMARY OF THE INVENTION

To achieve the foregoing and other objects, and in accordance with the purposes of the invention as broadly described herein, the present invention provides devices for vaporizing and delivering an agent in the form of an aerosol, referred to herein as "an aerosol agent." In the exemplary embodiments shown and described herein, the aerosol agent delivery devices provide a portable, effective, convenient, easy to use device for reliably and repeatedly vaporizing and delivering a wide range of aerosol agents, for example a therapeutic drug in the form of an aerosol to a patient, or nicotine in the form of an aerosol to a smoker.

In one exemplary embodiment, the invention is a handheld, portable torch for vaporizing an aerosol agent and delivering the aerosol agent to a user. By way of example and not limitation, the handheld torch may be used to vaporize and deliver a therapeutic drug in the form of an aerosol to a patient, or alternatively, nicotine in the form of an aerosol to a smoker. Broadly, the torch includes a heat generator operably coupled with a heat conductor defining a heat conducting chamber, and a generally hollow substrate holder operably coupled with the heat conducting chamber. The heat conductor has a first opening for receiving a heating element of the heat generator and for communicating heat generated by the heat generator to the heat conducting chamber. The heat conductor has a second opening for receiving an end of the substrate holder in heat conducting relation with the heat conducting chamber. The heat conductor has a third opening for allowing ambient air to be drawn through the heat conductor and the substrate holder when a user inhales on an opposite open end of the substrate holder. The heat generator is activated to ignite the heating element and thereby generate heat within the heat conductor that is communicated into the heat conducting chamber. The heat within the heat conducting chamber is conducted to a substrate disposed within the substrate holder that supports at least the aerosol agent and an aerosol forming agent. The conducted heat vaporizes the aerosol agent from the substrate to form an aerosol that is available along with ambient air to be inhaled by the user through the open end of the substrate holder.

The heating element of the heat generator of utilizes a fuel source consisting essentially of a combustible liquefied gas to generate heat. The combustible liquefied gas preferably is selected from liquefied petroleum gas (LPG or LP-gas), propane, propylene, butylenes, butane, isobutene, methyl propane and n-butane. The substrate may be any heat absorbing material that is non-combustible at the temperature of the heat conducted to the substrate. By way of example and not limitation, the substrate may be formed of a semi-porous cellulose paper material or a finely woven wire mesh material having the aerosol agent and the aerosol forming agent applied to the substrate material. The aerosol forming agent is a polyol preferably selected from glycerin, glycerol, propylene glycol, 1,3-butylene glycol, triethylene glycol, glycryl esters, such as triacetin, propylene carbonate, and mixtures thereof. The aerosol agent may be a therapeutic drug in the form of a heat stable pharmaceutical having less than about 10% alteration and/or degradation under normal transport and storage conditions for treatment of a patient. Alternatively, the aerosol agent may be nicotine for inhalation by a smoker.

In another exemplary embodiment, the invention is a handheld, portable, battery-powered aerosol agent delivery device for vaporizing an aerosol agent and delivering the aerosol agent to a user. By way of example and not limitation, the aerosol agent delivery device may be used to vaporize and deliver a therapeutic drug in the form of an aerosol to a patient, or alternatively, nicotine in the form of an aerosol to a smoker. Broadly, the aerosol agent delivery device includes a heat generator operably coupled in heat conducting relation with a generally hollow substrate holder. The substrate holder includes an end that is inserted into the heat generator in fluid communication with the ambient air and an opposite open end configured for use by a user to inhale the aerosol agent along with the ambient air. The heat generator includes a heating element disposed about the substrate holder and having an electrical connection with a battery. The heating element generates heat when electrically connected to the battery by a switch. Heat from the heating element is conducted to a substrate disposed within the substrate holder that supports at least the aerosol agent and an aerosol forming agent. The heat vaporizes the aerosol agent from the substrate to form an aerosol that is available to be inhaled by the user along with the ambient air through the open end of the substrate holder.

If desired, the aerosol agent delivery device may further include an auxiliary heat generator positioned adjacent the substrate disposed within the substrate holder. The auxiliary heat generator includes a generally hollow housing having an open end in fluid communication with the ambient air and an opposite end that is partially closed by an auxiliary heating element. The auxiliary heating element is electrically connected to the battery of the heat generator to produce an electrical current therethrough. Accordingly, the auxiliary heating element generates heat when electrically connected to the battery by the switch of the heat generator. Heat from the auxiliary heating element is conducted to the substrate disposed within the substrate holder adjacent the auxiliary heat generator that supports at least the aerosol agent and the aerosol forming agent. The heat generated by the auxiliary heating element, either alone or in combination with the heat generated by the heating element of the heat generator and likewise conducted to the substrate, vaporizes the aerosol agent from the substrate to form an aerosol that is available to be inhaled by the user along with the ambient air through the open end of the substrate holder.

BRIEF DESCRIPTION OF THE DRAWINGS

These and other features, aspects and advantages of the invention are better understood and appreciated when considered in light of the following detailed description of the invention with reference to the accompanying drawings.

FIG. 14A illustrates a substrate material for forming a substrate suitable for use with a device constructed according to the invention.

FIG. 14B illustrates another substrate material for forming a substrate suitable for use with a device constructed according to the invention.

FIG. 14C illustrates another substrate material for forming a substrate suitable for use with a device constructed according to the invention.

FIG. 14D illustrates another substrate material for forming a substrate suitable for use with a device constructed according to the invention.

DETAILED DESCRIPTION OF THE INVENTION

The invention will be described more fully hereinafter with reference to the accompanying drawings in which one or more exemplary embodiments are shown. However, it is to be understood that the invention may be embodied in many different forms and should not be construed as limited to the exemplary embodiments set forth herein. Exemplary embodiments of the invention are provided herein so that this disclosure will fully and completely convey the broad scope of the invention and to enable one of ordinary skill in the art to make, use and practice the invention without undue experimentation. Like reference numbers in the description and accompanying drawing figures refer to the same or similar elements of the invention.

The exemplary embodiments provided herein show and describe devices for vaporizing and delivering an agent in the form of an aerosol, also referred to herein as an "aerosol agent," to a user. As used herein, the term "aerosol" is intended to include vapors, dense gases, fine suspended particles, and the like, both visible and invisible. As so defined, "aerosol" specifically includes any pharmacologically or physiologically active agents, and any desired additives, such as an aerosol forming agent, irrespective of whether they produce a visible aerosol. Ideally, the aerosol has a density consistent with cigarette smoke and a small particle size on the order of about 0.2-3.0 microns. As used herein, the term "aerosol drug" refers to a therapeutic drug in the form of an aerosol available for delivery to a patient for use in inhalation therapy. Similarly, the term "aerosol nicotine" refers to nicotine in the form of an aerosol available for delivery to a smoker for use in smoking a combustion-free electronic cigarette, commonly referred to as a "smokeless cigarette," "e-cigarette" or "e-cig." The aerosol agent, and more specifically the aerosol drug or the aerosol nicotine, is preferably formed by an aerosol forming agent activated by heat generated by a heating element and conducted by a heat conductor. An aerosol agent delivery device for vaporizing and delivering an aerosol agent according to the invention provides a portable, effective, convenient, simple to use device for reliably and repeatedly vaporizing and delivering a wide range of aerosol agents to a user. Such devices may be particularly useful for vaporizing and delivering a therapeutic drug in the form of an aerosol drug to a patient, or alternatively, nicotine in the form of aerosol nicotine to a smoker.

Figure 1:
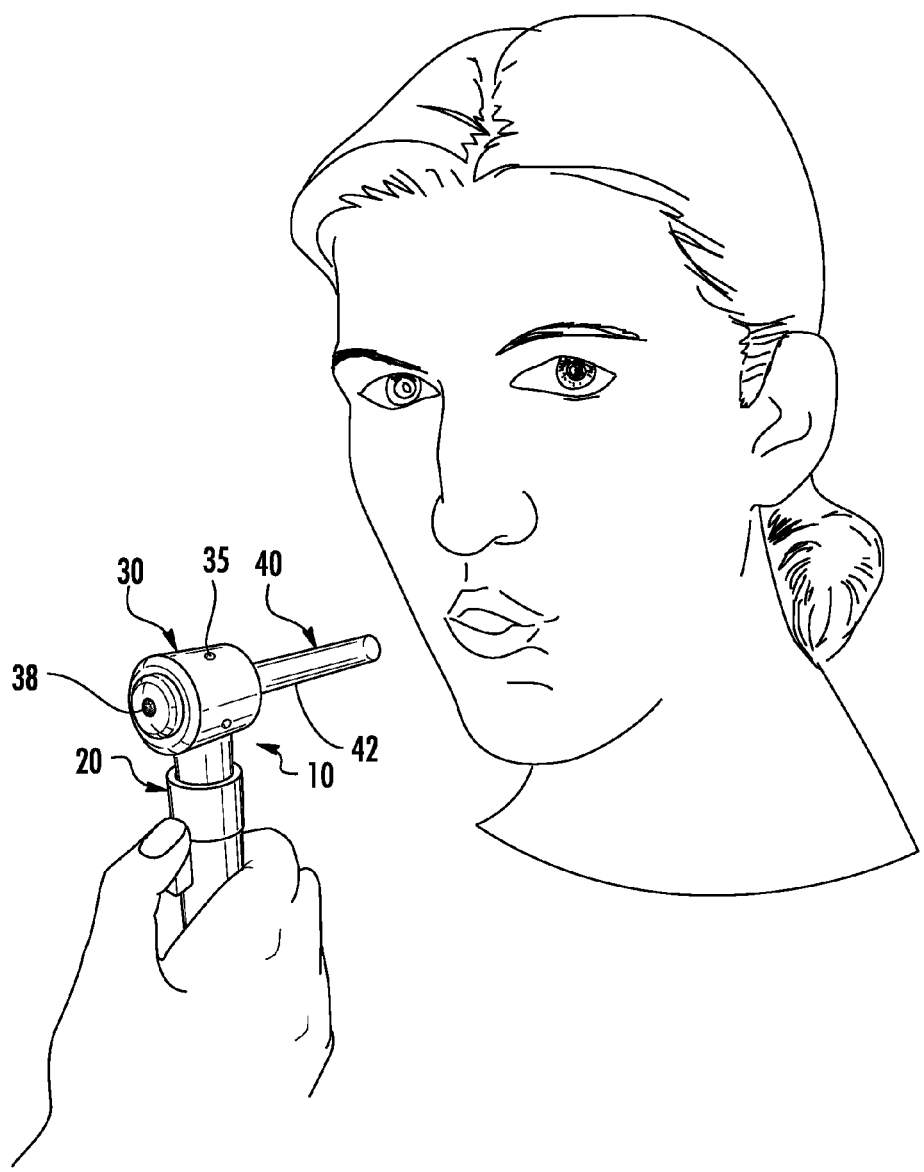
FIG. 1 is an environmental perspective view of an exemplary embodiment of a device for vaporizing and delivering an aerosol agent to a user constructed according to the invention illustrating the user utilizing the device to inhale the aerosol agent.
Figure 2:
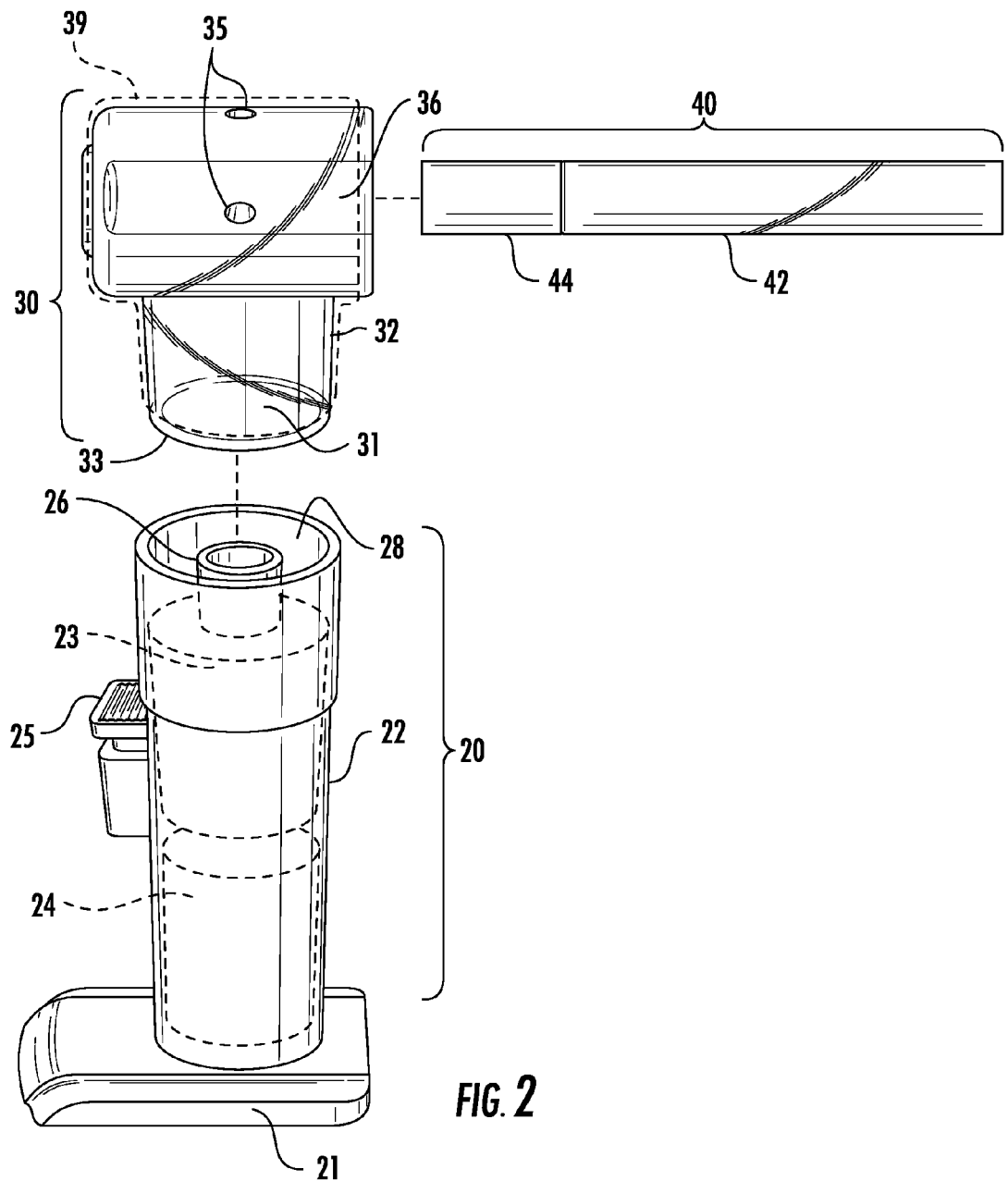
FIG. 2 is an exploded partial perspective view showing the heat generator, the heat conductor and the substrate holder of the device of FIG. 1 in a disassembled configuration.
Figure 3:
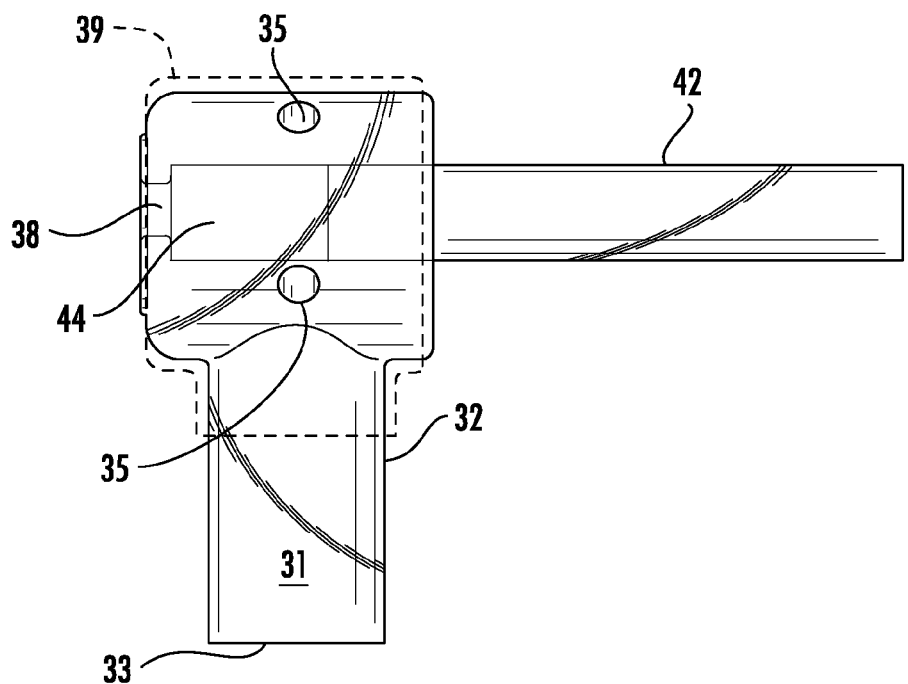
FIG. 3 is an elevation view showing the heat conductor and the substrate holder of the device of FIG. 1 in an assembled configuration.
Figure 4:
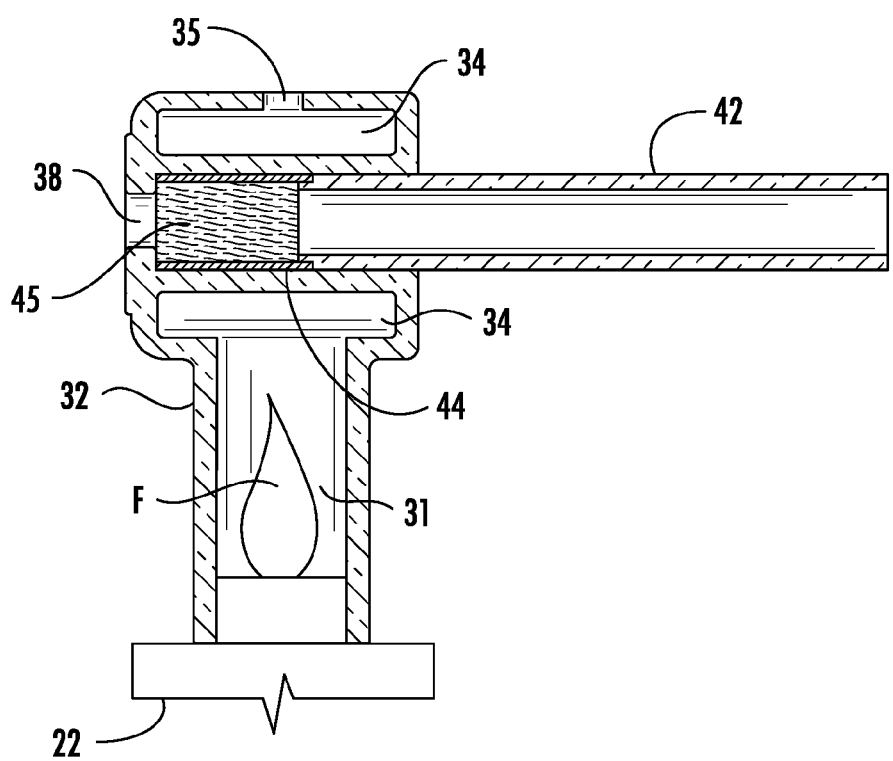
FIG. 4 is a partial sectional view of the device of FIG. 1.

An environmental perspective view of an exemplary embodiment of a device 10 for vaporizing and delivering an aerosol agent according to the invention is shown in FIG. 1. FIG. 2 is an exploded perspective view showing the device 10 disassembled. The device (also referred to herein as an aerosol agent delivery device) 10 comprises a heat generator 20, a heat conductor 30 and a substrate holder 40. FIG. 3 is an elevation view showing the heat conductor 30 and the substrate holder 40 assembled. FIG. 4 is a partial sectional view of the device 10 showing the heat conductor 30 and the substrate holder 40 in greater detail.

The heat generator 20 may be any means for reliably and repeatedly generating a relatively clean source of heat. As shown and described herein, the heat generator 20 is a handheld, portable torch. In a particularly advantageous embodiment, the heat generator 20 is a modified form of a commercially available micro butane torch that is capable of generating a localized flame of up to about 2400° F. Examples of a suitable micro butane torch include the BernzOmatic Micro Flame Butane Torch, the Weller ML100 Magna-Lite Butane Torch, and the Blazer PT-4000 Pencil Butane Torch. The specific type, style and brand of the heat generator 20, however, are not considered essential to the invention. Regardless, an existing heat generator 20 that has proven to be suitable to achieve the primary objectives of the invention is a Weller® Portasol® PSI 100 handheld butane heat torch available from Cooper Tools of Apex, N.C. "Weller" is a registered trademark of Cooper Industries, Inc., and "Portasol" is a registered trademark of Oglesby and Butler Ltd.

As best shown in FIG. 2, the heat generator 20 comprises a generally hollow housing 22 configured to contain an ignition system 23, for example a piezo electronic igniter, a heating element 24 and a switch 25 electrically connected to the ignition system for igniting the heating element. If desired, the heat generator 20 may also comprise a base, or stand, 21 for supporting the aerosol agent delivery device 10 in an upright orientation. The heating element 24 comprises a fuel source consisting essentially of a combustible liquefied gas that generates heat when ignited by the igniter 23 in response to activation of the switch 25. The combustible liquefied gas preferably is selected from liquefied petroleum gas (LPG or LP-gas), propane, propylene, butylenes, butane, isobutene, methyl propane and n-butane. The combustible liquefied gas comprises hydrocarbons, and in particular, aliphatic hydrocarbons such as carbon alkenes, which are gases at normal atmospheric temperatures and pressures, but are typically compressed to a liquid for storage and transport. Such a combustible liquefied gas is readily available, economical to use and burns cleanly as compared to carbonaceous and fossil fuels. When ignited in the presence of sufficient oxygen, the combustible liquefied gas burns to produce essentially water vapor ($H_2O$) and carbon dioxide ($CO_2$). When free oxygen is limited, the ignited combustible liquefied gas also produces small amounts of carbon soot and carbon monoxide (CO). As a result, there is little or no opportunity for the user to inadvertently inhale any harmful or unhealthy by-products or combustion gases produced from ignition of the heating element 24.

As previously mentioned, the heat generator 20 may be any suitable device or apparatus for generating heat from a combustible liquefied gas. Preferably, however, the heat generator 20 is sufficiently small and lightweight to be held by the user in one or both hands during vaporization and delivery of the aerosol agent. The entire aerosol agent delivery device 10, including the heat generator 20, the heat conductor 30 and the substrate holder 40 should be small enough and sufficiently lightweight to be portable so that a user can conveniently transport and use the device in any location. Activating (for example, by depressing) the switch 25 causes the igniter 23 to ignite the heating element 24 and produce a high temperature open flame F (FIG. 4) adjacent a heat discharge end, or tip, 26 of the heat generator 20. Conversely, deactivating (for example, by releasing) the switch 25 extinguishes the open flame F adjacent the tip 26 of the heat generator 20. If desired, the heating element 24 may be removable from the housing 22 of the heat generator 20 for safe storage, as well as for the purpose of replacing an expendable heating element. As shown in FIG. 2, the housing 22 and the tip 26 of the heat generator 20 define an annular recess 28 for receiving the heat conductor 30 in a permanent connection, or alternatively, in a temporary relatively tight interference fit attachment, as will be described hereinafter.

The heat conductor 30 comprises a generally hollow housing 32 configured to be received within the recess 28 defined by the heat generator 20. Housing 32 defines a first opening, or recess, 31 at one end adapted for receiving the heat discharge end, or tip, 26 of the heat generator 20 such that the flame F is disposed within the recess 31 of the heat conductor 30 (FIG. 4). As shown, recess 31 is bounded by an annular lip 33 that is configured to removably cooperate with the recess 28 defined by the housing 22 and the tip 26 of the heat generator 20 in a relatively tight interference fit. In this manner, heat generator 20 and heat conductor 30 are separable for replacement, repair, maintenance and/or cleaning as needed, yet are securely attached so as to remain in physical contact with one another in an airtight connection during use. Regardless, recess 31 is in fluid (i.e. airflow) communication with an internal heat conducting chamber 34 (FIG. 4) defined by the housing 32 of heat conductor 30. More particularly, housing 32 defines a relatively thin, double-walled, annular chamber 34 that is in heat communicating relation with recess 31 of heat conductor 30. As a result, heat generated by the heating element 24 of heat generator 20 is communicated from the recess 31 defined by housing 32 into annular heat conducting chamber 34. Combustion gases and excess heat generated by heat generator 20 are expelled from the annular heat conducting chamber 34 and absorbed into the ambient atmosphere through a plurality of vent holes 35 formed through the outer wall of the housing 32 of the heat conductor 30 at circumferentially spaced apart locations.

Housing 32 of heat conductor 30 further defines a second opening, or recess, 36 (FIG. 2) configured for receiving an end of the substrate holder 40. It should be noted that in the exemplary embodiments shown and described herein the recess 36 does not extend through the entire longitudinal length of the housing 32 of heat conductor 30. Instead, recess 36 terminates adjacent, but slightly spaced from, the opposite side of the housing 32 so that the substrate holder 40 cannot pass through the heat conductor 30 if inserted too far into housing 32. As will be readily appreciated by those skilled in the art, it is preferred that the outer surface of the substrate holder 40 forms a slight interference fit with the inner surface of the housing 32 of heat conductor 30 that defines recess 36. By way of example and not limitation, the diameter of recess 36 may be tapered in a decreasing manner along the longitudinal length of the recess from the outside of housing 32 in the direction of the interior of the housing. In this manner, the end of the substrate holder 40 will remain securely engaged with the heat conductor 30 when the substrate holder is inserted into the recess 36, as will be described. Heat conductor 30 and/or substrate holder 40 may be made of any substantially rigid material, such as metal, hard plastic, ceramic, glass or the like. In an advantageous embodiment, the heat conductor 30 and/or the substrate holder 40 are formed from Pyrex® glass of the type available from Sigma-Aldrich Company of St. Louis, Mo., or R&H Filter Co., Inc. of Georgetown, Del. "Pyrex" is a registered trademark of Corning, Incorporated of Corning, N.Y.

As shown, housing 32 of heat conductor 30 further defines a third opening, or recess, 38 opposite and in fluid (i.e. airflow) communication with recess 36. Recess 38 is also in fluid (i.e. airflow) communication with the ambient atmosphere such that ambient air can be drawn via recess 38 into and through the hollow substrate holder 40 that is aligned with the recess 38 when the end of the substrate holder 40 is positioned within the recess 36. Alternatively, recess 38 may be substituted by a plurality of smaller diameter openings each likewise being in fluid (i.e. airflow) communication with the ambient atmosphere and with recess 36 defined by housing 32. Regardless, it is important to note that the overall size (e.g. cross-sectional area and diameter) of the recess 38 is smaller than the overall size (e.g. cross-sectional area and diameter) of the recess 36 so that the end of the substrate holder 40 disposed within the recess 36 cannot pass through the recess 38 formed in the housing 32 of the heat conductor 30, as previously mentioned.

If desired, at least a portion of the housing 32 of the heat conductor 30 may be covered by a heat insulator 39, such as ceramic, insulating plastic or the like, so as to reduce the temperature generated by the heat generator 20 on the exterior surface of the housing. A known heat insulator 39 that can be employed in practicing the invention is a porous, resilient jacket formed from one or more layers of an insulating material. Alternatively, the heat insulator 39 could be an expanded metal jacket with or without perforations that is attached to the heat conductor 30 and may be spaced from the exterior surface of the housing 32 by an air gap. Preferably, the heat insulator 39 extends over substantially the entire outer periphery of the housing 32 of the heat conductor 30. Insulating materials which can be used in accordance with the present invention generally comprise inorganic or organic fibers such as those made out of glass, alumina, silica, vitreous materials, mineral wool, carbons, silicon, boron, organic polymers, cellulosics, and the like, including mixtures of these materials. Nonfibrous insulating materials, such as silica aero gel, pearlite, glass, and the like, formed in mats, strips or other shapes can also be used. Preferred insulating materials should have a softening temperature below about 650° C. and should not burn, char or decompose during use. Preferred insulating materials for the heat conductor 30 (and similarly the housing 22 of the heat generator 20) include ceramic fibers, such as glass fibers available from the Manning Paper Company of Troy, N.Y., under the commercial designations Manniglas 1000 and Manniglas 1200.

As shown, substrate holder 40 comprises an elongate, cylindrical, generally hollow aerosol delivery tube 42 having an end configured to be received within the recess 36 formed in the heat conductor 30. As previously mentioned, the end of the substrate holder 40 preferably engages the recess 36 in an interference fit so that the substrate holder and the heat conductor 30 are securely attached to one another during use. Alternatively, the end of the substrate holder 40 and the recess 36 may be provided with a spiral groove and cooperating thread, a light adhesive or any other means suitable for removably securing the end of the substrate holder to the housing 32 of the heat conductor 30. As shown herein, substrate holder 40 further comprises an annular heat sink 44 adjacent and circumferentially disposed about the end of the aerosol delivery tube 42 that is inserted into the recess 36 of the heat conductor 30. The heat sink 44 is made of any solid or semi-porous, non-combustible, thermally conductive material suitable for transferring heat from the annular heat conducting chamber 34 into a substrate 45 (FIG. 4) disposed within the substrate holder 40. By way of example and not limitation, the heat sink 44 may be a relatively thin, annular ring made of a thermally conductive metal or an impervious silicon or ceramic. Alternatively, the heat sink 44 may be a somewhat thicker ring formed from a cellulose material. In other instances, the heat sink 44 may be a finely woven wire mesh or perforated metal ring. Typically, however, the selection of the thermal conductivity, porosity, thickness and material of the heat sink 44 will be determined by the volatility of the aerosol agent and the aerosol forming agent utilized with the device 10.

Regardless, the heat sink 44 is operable to transfer the heat generated by the heat generator 20 and communicated to the annular heat conducting chamber 34 by the heat conductor 30 to the substrate 45 disposed within the substrate holder 40. The heat sink 44 is in heat conducting relation with the annular heat conducting chamber 34 and with the substrate 45 to transfer heat from the heat conducting chamber to the substrate by conduction or convection means readily understood and appreciated by those having ordinary skill in the art. In some instances, the heat sink 44 is further operable to support the substrate 45 within the substrate holder 40. By way of example and not limitation, the heat sink 44 is a non-combustible, thermally conductive metal ring that is in direct physical contact with the inner wall of the housing 32 that defines the annular heat conducting chamber 34. As a result, heat generated by the heating element 24 of the heat generator 20 and communicated to the annular heat conducting chamber 34 of the heat conductor 30 is transferred through the inner wall of the housing 32 into the heat sink 44, and subsequently transferred from the heat sink into the substrate 45.

As best shown in FIG. 4, the substrate holder 40 further comprises the substrate 45 that is disposed within the hollow aerosol delivery tube 42 generally concentric with the annular heat sink 44. The substrate 45 is disposed within the aerosol delivery tube 42 in heat conducting relation with the heat sink 44. In other words, the substrate 45 is in direct physical contact with the heat sink 44, or is immediately adjacent the heat sink so that heat (i.e., thermal energy) generated by the heating element 24 and communicated to the annular heat conducting chamber 34 is transferred across the inner wall of the housing 32 to the heat sink and conducted into the substrate. The substrate 45 may be made of any suitable thermally stable material having sufficient surface area and/or porosity to contain the aerosol agent and the aerosol forming agent, and furthermore, to permit vaporization aerosol formation by the application of heat. As used herein, "thermally stable" is intended to mean capable of withstanding the high temperatures (e.g., about 200° C. to about 600° C.) generated by the heating element 24 of the heat generator 20, transferred by the heat conducting chamber 34 to the heat sink 44 and conducted into the substrate 45 without causing decomposition or burning of the material of the substrate. Useful thermally stable materials include thermally stable adsorbent carbons, such as porous grade carbons, graphite, activated or non-activated carbons, carbon fibers, carbon yarns, and the like. Other suitable materials include inorganic solids such as ceramics, glass, aluminum pellets, alumina, vermiculite, clays such as bentonite, and the like. In the exemplary embodiments shown and described herein, the substrate 45 is made from a cellulose-based paper material and/or a metal wire formed as a finely woven wire mesh or screen.

The substrate 45 may have any desired size and shape sufficient to contain at least a single dosage amount of the aerosol agent and enough aerosol forming agent to volatilize (i.e. vaporize) the aerosol agent in the form of an aerosol. In an advantageous embodiment, the substrate 45 is generally cylindrical and formed from a cellulose-based paper material suitable for low temperature vaporization and aerosol formation at temperatures below the decomposition threshold of cellulose. By way of example and not limitation, the substrate 45 may be a semi-porous cellulose paper of the type commercially available from EMI Specialty Papers, Inc. of Redding, Conn. The cellulose paper is impregnated with a liquid mixture of the aerosol agent and the aerosol forming agent, or alternatively, the liquid mixture is deposited on the cellulose paper and absorbed. In another advantageous embodiment, the substrate 45 is made of a metal wire material formed as a finely woven wire mesh comprising one or more layers of wire mesh weaves. An example of such a substrate 45 is a metal filter available from G. BOPP USA, Inc. of Hopewell Junction, N.Y., commercially known as Twilled Dutch Weave Wire Cloth having a 510×3600 warp to weft weave with a warp wire diameter of about 0.025 mm and a weft wire diameter of about 0.015 mm. The preferred BOPP Twilled Dutch Weave Wire Cloth has a nominal filter rating of less than about 1 micron and an absolute filter rating of between about 5 and about 6 microns. The Twilled Dutch Weave Wire Cloth provides extremely small openings to maximize heat conduction and convection, while increasing the surface area available for deposition of the aerosol agent and the aerosol forming agent by as much as 8-fold. The specific weave and warp/weft wire diameter of the metal filter cloth, however, is determined by the optimum delivery characteristics of a particular aerosol agent, and in particular, the boiling point, vaporization rate and aerosol formability of the combination aerosol agent and aerosol forming agent.

Regardless of the material, the outer periphery of substrate 45 is preferably in direct contact with the annular heat sink 44 to provide a heat transfer relation between the heat conductor 30 and the substrate containing the aerosol agent and the aerosol forming agent. Thus, heat transfer to the substrate 45 and the resultant production of the aerosol agent for delivery to the user in the form of an aerosol is maximized. Because the aerosol agent and the aerosol forming agent are physically separated from the heating element 24 of the heat generator 20 by the annular heat conducting chamber 34 and the annular heat sink 44, the agents are exposed to a lower temperature than the open flame F generated by the heating element within the recess 31 of the heat conductor 30. Accordingly, the possibility of thermal degradation of the aerosol agent is unlikely.

Figure 5:
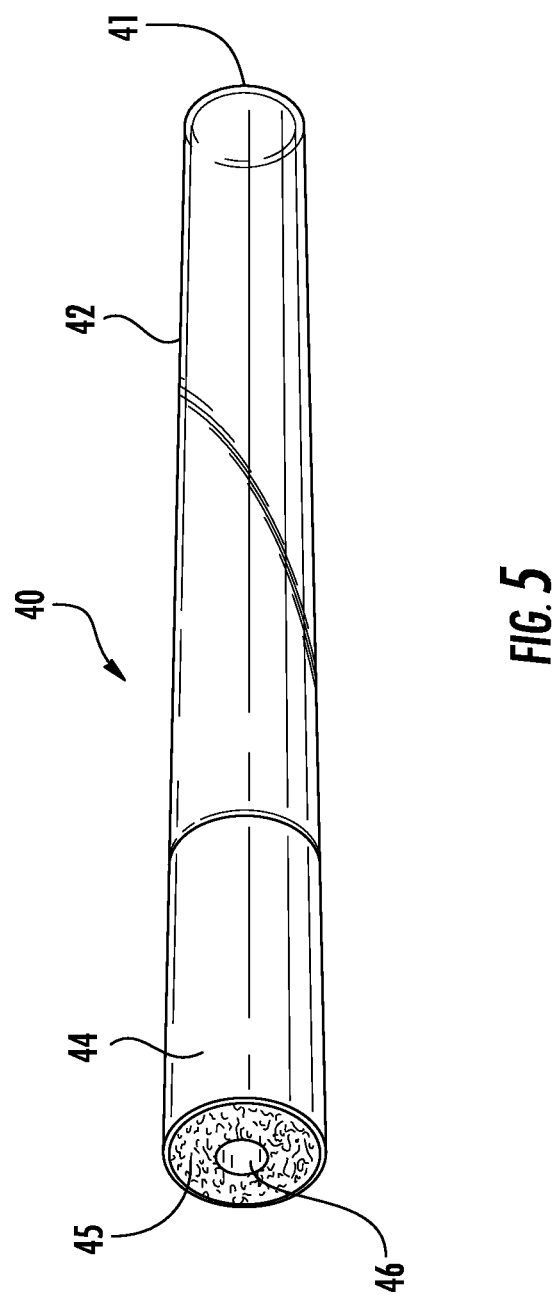
FIG. 5 is a detailed perspective view of the substrate holder of the device of FIG. 1.

FIG. 5 is a perspective view showing the substrate holder 40 in greater detail. As shown, the substrate 45 is inserted into the end of the substrate holder 40 and positioned adjacent and concentric with the heat sink 44. The opposite other end 41 of the aerosol delivery tube 42 is open to the ambient atmosphere and configured as a relatively small diameter cylinder to engage the mouth of the user (FIG. 1). Alternatively, the open end 41 of the aerosol delivery tube 42 may comprise an irregular shaped mouthpiece (not shown) sized to comfortably engage the mouth of the user. Regardless, the length of the aerosol delivery tube 42 and optional mouthpiece is selected so that the switch 25 of the heat generator 20 is located at a convenient distance from the user, while at the same time the heat generator 20 is sufficiently distant from the mouth of the user to limit the ambient temperature. As previously mentioned, the substrate 45 is made of semi-porous material, for example cellulose paper or finely woven wire mesh, so that the user can draw air from the ambient atmosphere through the recess 38 formed in housing 32 of heat conductor 30 and along the longitudinal length of the hollow aerosol delivery tube 42. As shown, a relatively small diameter hole 46 may be formed through the center of the substrate 45 to increase the amount of ambient air that the user is able to draw through the recess 38 and down the longitudinal length of the aerosol delivery tube 42, and consequently, significantly reduce the effort required of the user to deliver the aerosol agent to his or her lungs.

As previously described, the aerosol agent and the aerosol forming agent are deposited onto the substrate 45 so that the aerosol forming agent can subsequently volatilize the aerosol agent in the form of an inhalable aerosol, or vapor, when heat is applied to the substrate. The aerosol agent and the aerosol forming agent are preferably combined into an admixed solution that is impregnated into or deposited onto the substrate 45. Regardless, the admixed solution may be applied to the substrate 45 in any convenient and suitable manner using any conventional means or process. By way of example and not limitation, the admixed solution may be applied to the substrate 45 by coating, spraying, brushing, dipping, vapor deposition, electrostatic deposition, chemical deposition, or the like such that the admixed solution forms a relatively thin film on the substrate consisting essentially of the aerosol agent and the aerosol forming agent. The aerosol agent may be any thermally stable, non-combustible agent, for example a therapeutic drug or nicotine, capable of being aerosolized and delivered to a user for vapor inhalation. The aerosol forming agent may be any thermally stable, inert aerosol former and/or carrier that is capable of volatilizing the aerosol agent and forming a vapor suitable for delivery to a user of an aerosol agent delivery device according to the present invention. Aerosol forming agents useful in the present invention are capable of forming an aerosol at the temperatures present in the heat conducting chamber 34, transferred to the heat sink 44 and subsequently transferred into the substrate 45 when heat is generated by the heating element 24. Such agents preferably are composed of carbon, hydrogen and oxygen, but they can include other elements and/or compounds.

The aerosol forming agent can be in solid, semisolid, or liquid form. Substances having these characteristics include polyhydric alcohols, such as glycerine and propylene glycol, as well as aliphatic esters of mono-, di-, or poly-carboxylic acids, such as methyl stearate, dimethyl dodecandioate, dimethyl tetradecandioate, and others. Preferably, the aerosol forming agent is a polyhydric alcohol, or a mixture of polyhydric alcohols. By way of example, and without limitation, preferred aerosol formers include glycerin, glycerol, propylene glycol, 1,3-butylene glycol, triethylene glycol, glycerol esters, propylene carbonate, and mixtures thereof. As much as possible of the aerosol agent and the aerosol forming agent carried on the substrate 45 should be delivered to the user. Preferably, above about 50 weight percent, more preferably above about 80 weight percent, and most preferably above about 90 weight percent of the admixed solution is delivered to the user. The substrate 45 containing the admixed solution of the aerosol agent and the aerosol forming agent may be provided to the user separately from the device 10 as single-dose unit of the aerosol agent, for example a single-dose of a therapeutic aerosol drug to a patient, or alternatively, a single-dose of aerosol nicotine to a smoker. In addition, a plurality of substrates 45 may be provided to the user in the commonly used packaging commercially known as a "blister pack" with each substrate vacuum packaged, sealed and individually removable for insertion into the substrate holder 40 before the substrate holder is inserted into the recess 36 of the heat conductor 30.

Figure 6:
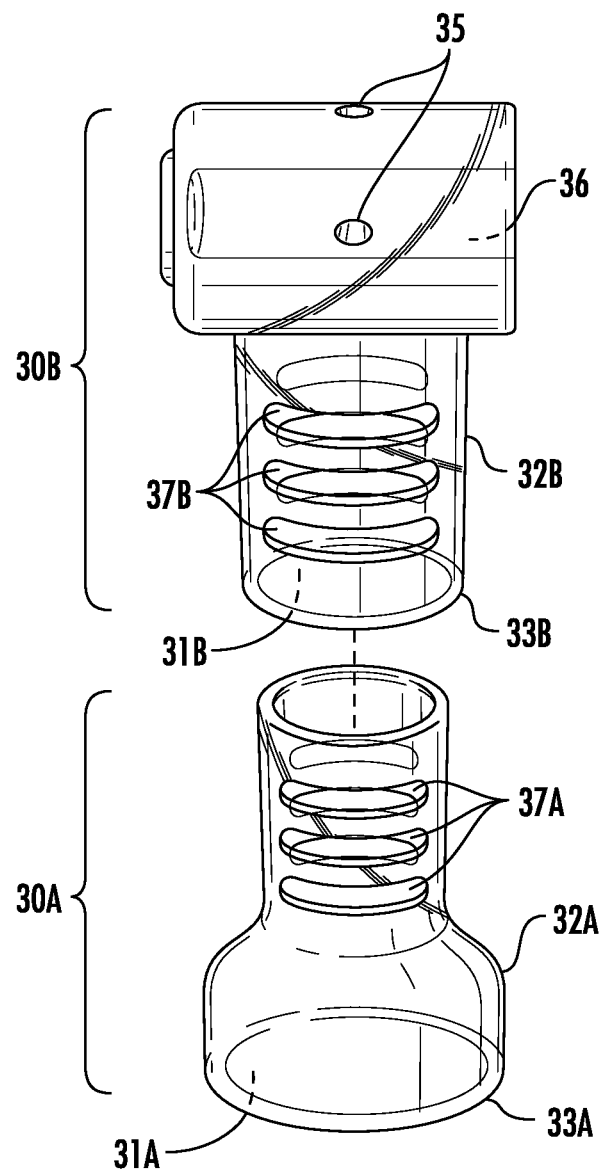
FIG. 6 is an exploded perspective view showing a coupler and an alternative heat conductor for use with the device of FIG. 1 in a disassembled configuration.
Figure 7:
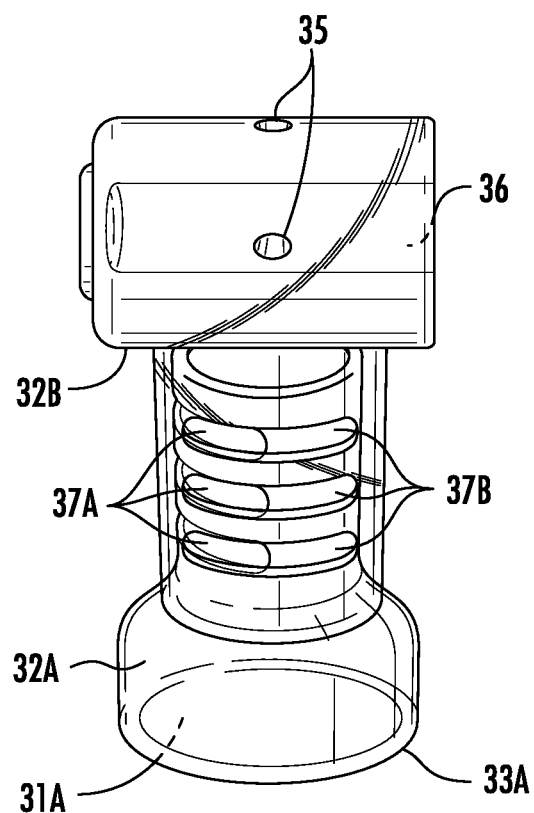
FIG. 7 is a perspective view showing the coupler and the alternative heat conductor of FIG. 6 in an assembled configuration.

FIG. 6 is a perspective view showing a coupler 30A and an alternative heat conductor 30B suitable for use with a device 10 according to the invention disassembled. The coupler 30A and the alternative heat conductor 30 are advantageous for use when the open flame F generated by the heating element 24 of heat generator 20 is subject to extinguishing due to an insufficient amount of oxygen (i.e. air) available within the recess 31 of the heat conductor 30 to sustain the flame. The coupler 30A comprises a generally hollow housing 32A having a lip 33A at one end that defines a recess 31A configured to receive the housing 22 of the heat generator 20. More specifically, housing 32A comprises an annular lip 33A at the one end that is sized and shaped to engage the outer surface of the cylindrical housing 22 of the heat generator 20 in a slight interference fit. Similarly, the alternative heat conductor 30B comprises a generally hollow housing 32B having a lip 33B at one end that defines a recess 31B configured to receive the opposite end of the housing 32A of the coupler 30A. More specifically, housing 32B comprises an annular lip 33B at one end that is sized and shaped to engage the outer surface of the housing 32A of the coupler 30A in a slight interference fit. Coupler 30A is provided with slotted openings 37A through the housing 32A and alternative heat conductor 30B is provided with like slotted openings 37B through the housing 32B. As shown in FIG. 7, openings 37A of housing 32A and openings 37B of housing 32B are aligned vertically and overlap to some extent when the coupler 30A and the alternative heat conductor 30B are assembled. The slight interference fit between the coupler 30A and the alternative heat conductor 30B may be overcome to rotate the housings 32A, 32B relative to one another, and thereby vary the extent of the overlap of the openings 37A, 37B. The extent of overlap of the openings 37A, 37B determines the amount of ambient air available to the open flame F of the heating element 24 of the heat generator 20. Increasing the extent of the overlap of the openings 37A, 37B correspondingly increases the amount of ambient air available to the open flame F disposed within the recess 31A of the coupler 30A.

Figure 8:
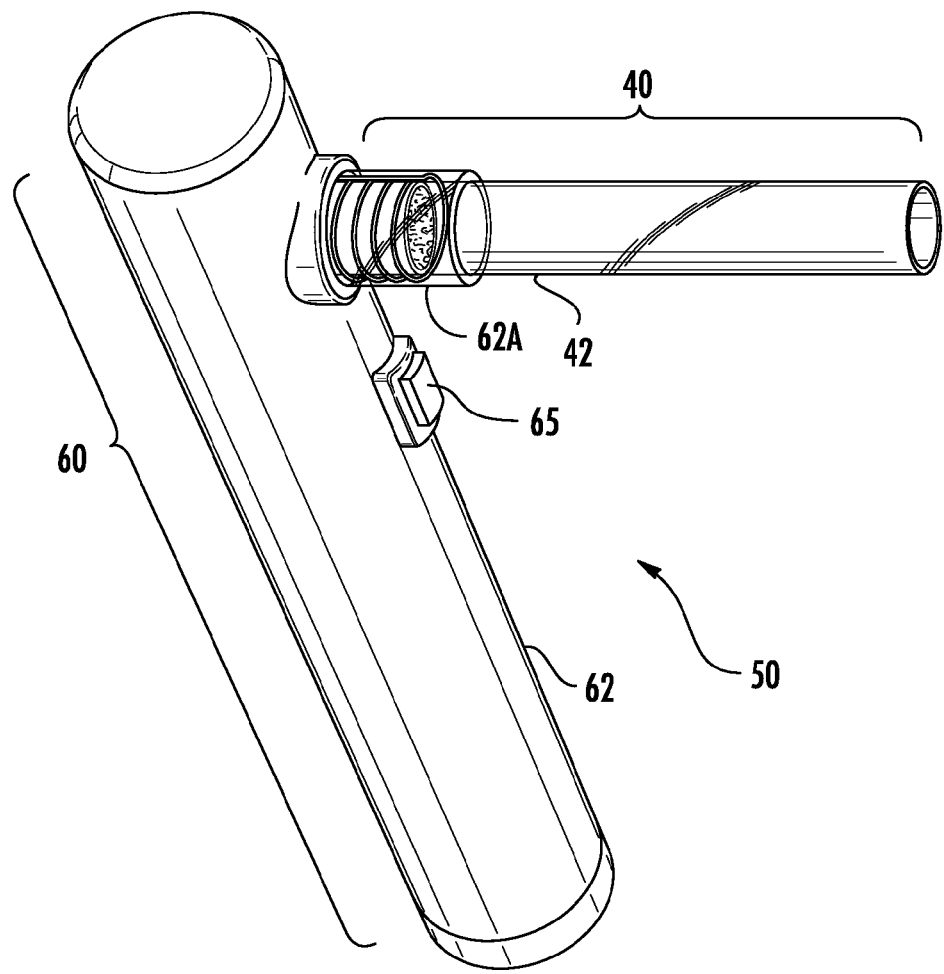
FIG. 8 is a perspective view of another exemplary embodiment of a device for vaporizing and delivering an aerosol agent constructed according to the invention.
Figure 9:
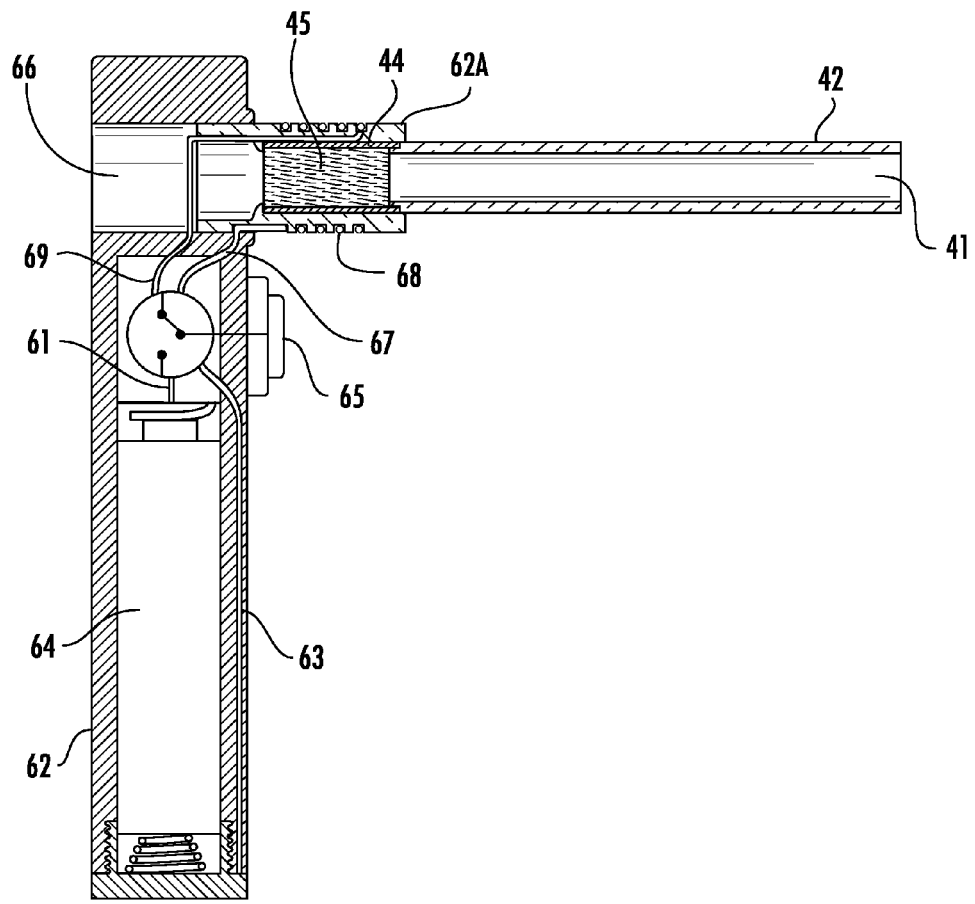
FIG. 9 is a sectional view of the device of FIG. 8.
Figure 10:
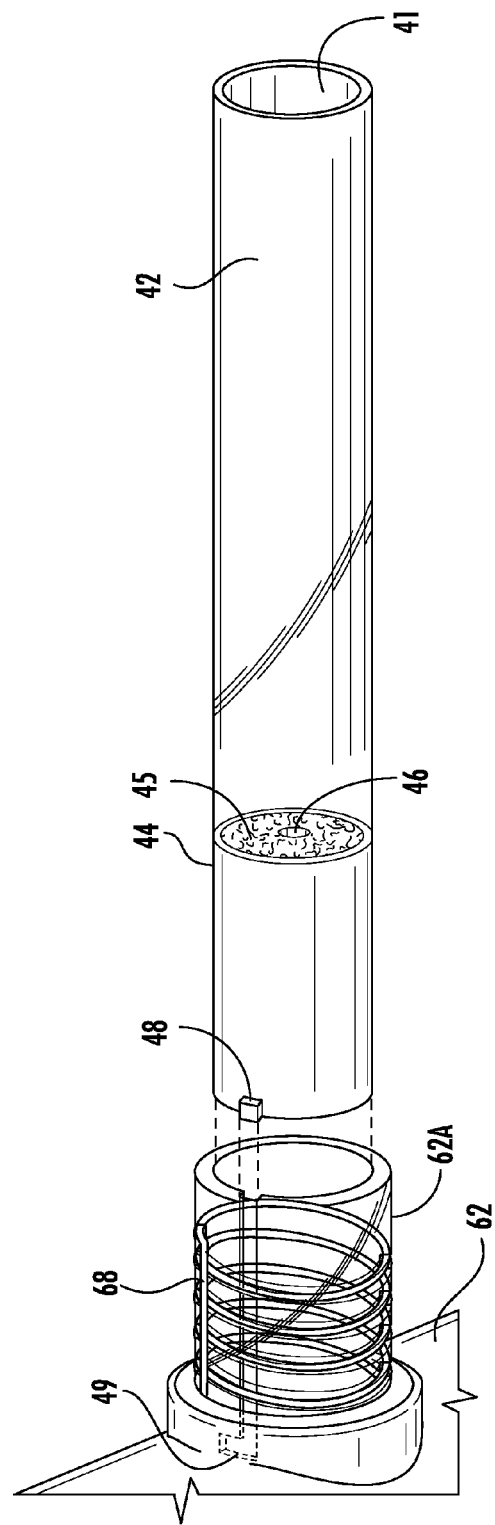
FIG. 10 is a detailed perspective view of the substrate holder and a receiver portion of the heat generator of the device of FIG. 8.

A perspective view of another exemplary embodiment of a device 50 for vaporizing and delivering an aerosol agent according to the invention is shown in FIG. 8. FIG. 9 is a sectional view of the device 50, while FIG. 10 is an enlarged perspective view of a portion of the device. The device (also referred to herein as an aerosol agent delivery device) 50 comprises a heat generator 60 and a substrate holder, such as the substrate holder 40 previously shown and described with respect to device 10. The heat generator 60 comprises a generally hollow housing 62 configured for containing a conventional battery 64 (FIG. 9) and the internal electronics of a switch 65 for activating a heating element 68 in heat conducting relation with the substrate 45 disposed within the substrate holder 40. As shown herein, a positive terminal of the battery 64 is electrically connected to the electronics of the switch 65 by a first power wire 61, while a negative terminal of the battery 64 is electrically connected to the electronics of the switch 65 by a second power wire 63. The heating element 68 may be any component, structure or material suitable for conducting heat generated by the heat generator 60 into the substrate 45 of the substrate holder 40. In a particularly advantageous embodiment, the heating element 68 comprises a nichrome heating coil made of a length of nichrome wire that is wound around an annular receiver 62A depending outwardly from the housing 62 of the heat generator 60. The exterior surface of the annular receiver 62A may be provided with a spiral groove for assisting to retain the nichrome wire on the receiver. Regardless, one end of the nichrome heating coil 68 is electrically connected to the electronics of switch 65 by a first heater wire 67, while the other end of the nichrome heating coil 68 is electrically connected to the electronics of the switch 65 by a second heater wire 69. As will be readily understood and appreciated by those skilled in the art, an electrical current flows through the nichrome heating coil 68 when switch 65 is activated (for example, by depressing the switch) to electrically couple the positive and negative terminals of the battery 64 between the heater wire 67 and the heater wire 69 of the nichrome heating coil.

The receiver 62A may be a structural extension of the housing 62 of the heat generator 60. Alternatively, the receiver 62A may be a separate cylindrical component that is permanently secured within a suitably sized and shaped recess formed in the housing 62. Regardless, receiver 62A defines an open end configured for receiving an end of the substrate holder 40 therein. As previously mentioned, one end of the aerosol delivery tube 42 of the substrate holder 40 is removably engaged with the open end of the receiver 62A of the heat generator 60. By way of example and not limitation, the end of the aerosol delivery tube 42 may engage the open end of the receiver 62A in a slight interference fit. Alternatively, the substrate holder 40 may be secured to the receiver 62A of the heat generator 60 by a tapered press fit, a temporary adhesive, a spiral groove and cooperating thread, or the like. As shown in FIG. 10, the end of the aerosol delivery tube 42 may also be provided with a locking tab 48 and the receiver 62A of the heat generator 60 may be provided with an L-shaped locking slot 49 such that the substrate holder 40 can be removably locked to the housing 62 of the heat generator 60 via the receiver 62A in the well known manner of a bayonet style lock. As previously described, the aerosol delivery tube 42 of the substrate holder 40 is preferably made of a substantially rigid material, such as metal, hard plastic, ceramic, glass or the like, and the open end 41 of the aerosol delivery tube may be provided with a mouthpiece. Furthermore, the end of the substrate holder 40 that is inserted into the receiver 62A of the heat generator 60 may also comprise the heat sink 44 for transferring heat produced by the nichrome heating coil 68 into the substrate 45. In yet another embodiment, the nichrome heating coil 68 may be replaced by the heat sink 44 and the heat sink eliminated from the substrate holder 40. In still another embodiment, the heating element 68 may comprise a relatively thin cylinder formed from the finely woven wire mesh previously described with reference to the substrate 45 that is attached to the inner or the outer surface of the receiver 62A by, for example, an adhesive. Regardless, the heating element 68 transfers heat generated by the heat generator 60 into the substrate 45 disposed within the substrate holder 40 and having at least an aerosol agent and an aerosol forming agent applied thereto.

As previously mentioned, and as illustrated in FIG. 10, the substrate 45 may be formed of cellulose-based paper impregnated with the aerosol agent and the aerosol forming agent. Furthermore, the substrate 45 may be provided with the longitudinally extending hole 46 for drawing ambient air from the surrounding atmosphere through the housing 62 and/or receiver 62A of the heat generator 60, and down the aerosol delivery tube 42 of the substrate holder 40 into the mouth of the user. Alternatively, the substrate 45 may be formed of the finely woven wire mesh previously described having the aerosol agent and the aerosol forming agent deposited thereon. If desired, a particle filter (not shown) may also be provided, for example within the receiver 62A between the housing 62 and the substrate 45, and/or between the substrate 45 and the open end 41 of the substrate holder 40. Such a particle filter would be useful to filter foreign particulate matter that may be present in the ambient air. Preferably, the particle filter comprises a screen configured to prevent the passage of particulate matter having a mean diameter greater than about 20 microns. In particular, the particle filter is intended to filter any un-vaporized particles of the aerosol agent or the aerosol forming agent and any combustion by-products that may be drawn along with the ambient air into the device 10 utilizing the micro butane torch heat generator 20 after being expelled from the annular heat conducting chamber 34 into the ambient atmosphere through the vent holes 35.

Figure 11:
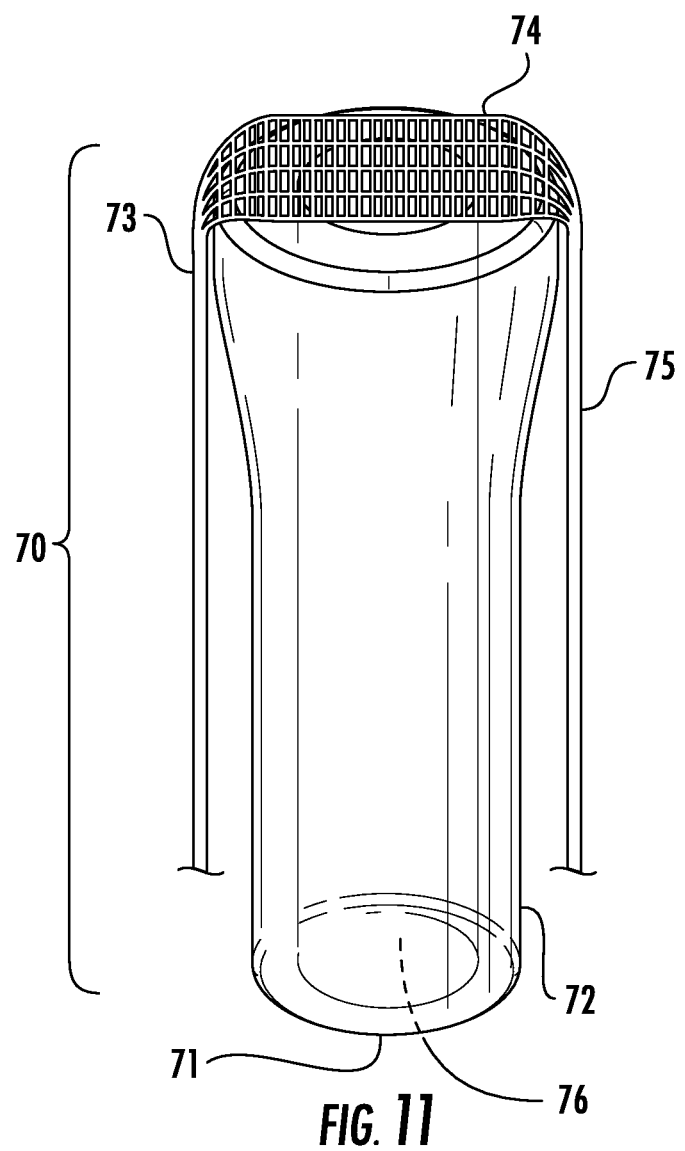
FIG. 11 is a detailed perspective view of an auxiliary heat generator for use with the device of FIG. 8.
Figure 12:
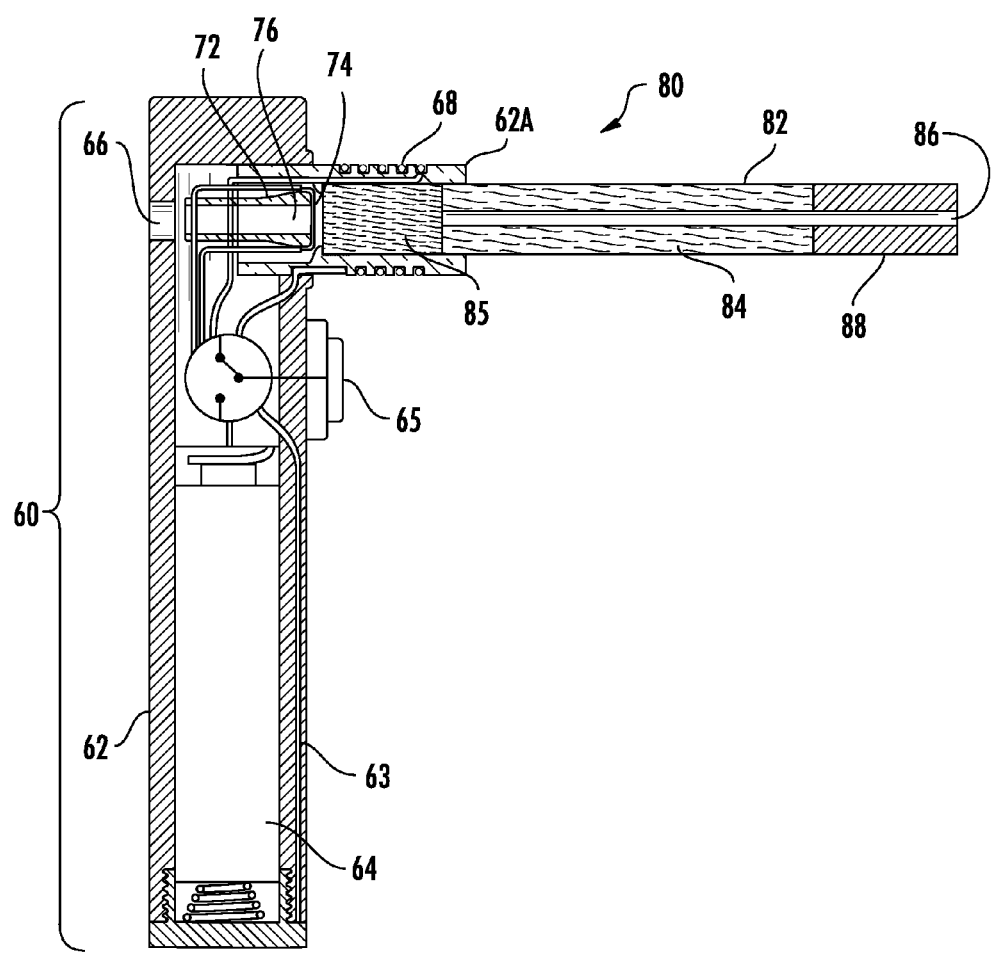
FIG. 12 is a sectional view of the device of FIG. 6 further including the auxiliary heat generator of FIG. 11.

FIG. 11 is an enlarged perspective view showing an auxiliary heat generator 70 for use with the device 50 described hereinabove. FIG. 12 shows a sectional view of the heat generator 60 as previously described further including the auxiliary heat generator 70 and operably coupled with an alternative embodiment of another substrate holder 80 suitable for use in the present invention. The auxiliary heat generator 70 comprises a generally hollow housing 72 made of a substantially rigid material, such as metal, hard plastic, ceramic, glass or the like. Housing 72 defines an annular lip 71 at one end configured to be loosely received within the receiver 62A of the housing 62 of heat generator 60 in alignment with a recess, 76 formed in housing 62 that is in fluid (i.e. airflow) communication with the ambient atmosphere. Auxiliary heat generator 70 comprises an auxiliary heating element 74 that is positioned adjacent the opposite other end of the housing 72. As shown, auxiliary heating element 74 is formed by a finely woven wire mesh having a first auxiliary heater wire 73 and a second auxiliary heater wire 75 for electrically connecting the woven wire mesh to the electronics of the switch 65 disposed within housing 62 of heat generator 60 in the manner previously described with respect to heater wire 67 and heater wire 69 of nichrome heating coil 68. As a result, electric current flows through auxiliary heating element 74 when switch 65 is activated (for example, by depressing the switch) to electrically couple the battery 64 to the auxiliary heating element 70. As shown, hollow housing 72 defines a longitudinally extending, axial opening, or recess, 76 for a purpose to be described hereinafter.

The substrate holder 80 is inserted into the receiver 62A of the housing 62 of heat generator 60 and secured in a suitable manner previously described. Similar to the substrate holder 40 discussed hereinabove, substrate holder 80 comprises an aerosol delivery tube 82 and a substrate 85 containing the aerosol agent and the aerosol forming agent. The auxiliary heating element 74 is located within receiver 62A adjacent to and in close proximity to the substrate 85. Thus, substrate 85 is simultaneously heated by both the heating element 68 of the heat generator 60 and the auxiliary heating element 74 of the auxiliary heat generator 70 when a user activates switch 65 (for example by depressing the switch). Heating the substrate 85, and more particularly, the aerosol agent and the aerosol forming agent applied to the substrate 85, causes the aerosol agent to be vaporized and made available to the aerosol delivery tube 82. As shown herein, the substrate holder 80 is provided with a longitudinally extending hole 86 that is axially aligned with the recess 76 formed in the hollow housing 72 of the auxiliary heat generator 70 and the recess 66 formed in the housing 62 of the heat generator 60 and in fluid communication with the ambient atmosphere. Accordingly, the aerosol agent is delivered to a user in the form of an aerosol when the user draws ambient air from the surrounding atmosphere through the recess 66, the recess 76, the substrate 85, and the hole 86 provided in the substrate holder 80. If desired, substrate 85 may be provided with a longitudinally extending through hole that is axially aligned with hole 86 of substrate holder 80 in the manner previously described with reference to hole 46 formed through substrate 45 of substrate holder 40. As will be readily appreciated, the substrate holder 80 including substrate 85 is intended to be removable from the receiver 62A of heat generator 60 for convenient storage and transport, as well as for the purpose of replacing an expendable substrate. Accordingly, substrate holder 80 including substrate 85 may be intended for a single use (i.e. disposable), and replaceable with a new substrate holder 80 including a new substrate 85 having an aerosol agent and an aerosol forming agent applied thereto for each use by a patient or smoker.

Figure 13:
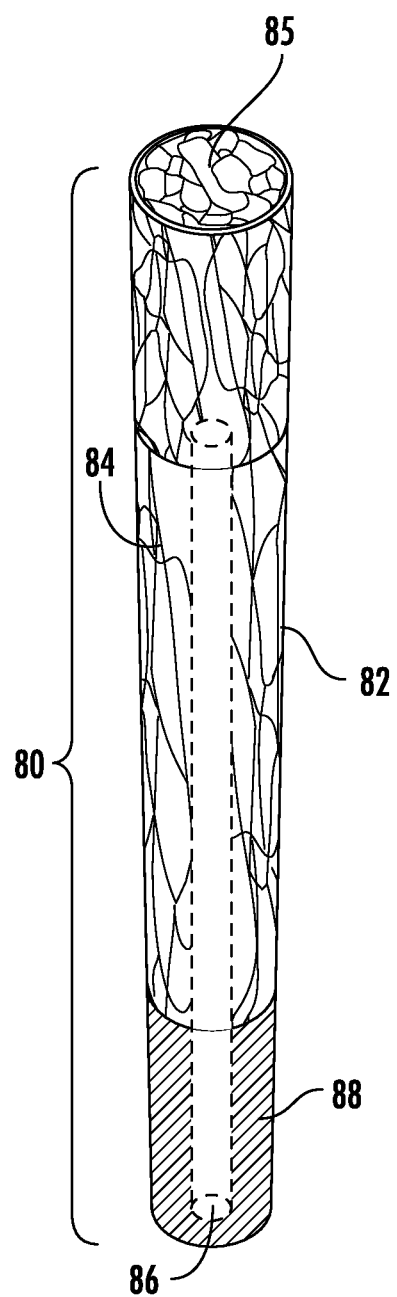
FIG. 13 is a perspective view of a substrate for use with a device constructed according to the invention.

FIG. 13 is a perspective view showing the substrate holder 80 illustrated in FIG. 12 for use with the auxiliary heat generator 70. The substrate 85 of the substrate holder 80 may comprise a shredded cellulose-based material, such as die-cut shredded paper. Alternatively, the substrate 85 may comprise an expanded starch-based material, such as puffed grain. Substrate 85 may also be formed of a combination of a cellulose-based material and an expanded starch-based material in a manner well known to those skilled in the art of conventional cigarette manufacture. As shown, the aerosol delivery tube 82 of the substrate holder 80 may further comprise a filler portion 84 adjacent the substrate 85 and an optional filter portion 88 adjacent the opposite end of the substrate holder, such that the filler portion 84 is medially disposed between the substrate 85 and the filter portion 88. Furthermore, the lengthwise, longitudinally extending hole 86 may also be formed through the filler portion 84 and through the filter portion 88. Hole 86 functions to increase the amount of ambient air that the user is able to draw through the recess 66 formed in housing 62 of heat generator 60, the recess 76 of the auxiliary heat generator 70, substrate 85 and aerosol delivery tube 82, and thereby significantly reduce the amount of effort required to deliver the aerosol agent to the user's lungs in the manner previously described with reference to hole 46 formed through substrate 45 of substrate holder 40. If desired, hole 86 may likewise extend through substrate 85 in the same manner that hole 46 extends through substrate 45. Filler portion 84 may be made of a version of the shredded cellulose-based material and/or expanded starch-based material of the substrate 85 having a significantly reduced density. Conversely, filter portion 88 may be made of a similar material as the substrate 85 having a somewhat greater density. The aerosol delivery tube 82 containing substrate 85, filler portion 84 and filter portion 88 may be formed from a cellulose-based material, such as thin film paper, in the same manner as the wrapping of a conventional cigarette. In addition, the substrate holder 80 may further include a heat sink 44 made of a thermally conductive material, such as a cylindrical metal band or a finely woven wire mesh screen in the form of a hollow cylinder, disposed concentrically about the substrate 85, as previously described with reference to substrate holder 40.

FIGS. 14A-14D illustrate examples of materials that may be utilized to form the substrate 45 of substrate holder 40 or the substrate 85 of substrate holder 80 shown and described herein. FIG. 14A illustrates strips or shreds of an expanded starch-based material and/or cellulose-based material 92 that forms the substrate 45, 85. FIG. 14B illustrates nuggets, chips or shards of an expanded starch-based material and/or cellulose based material 94 that forms the substrate 45, 85. FIG. 14C illustrates a relatively thin sheet, layer or film of an expanded starch-based material and/or cellulose-based material 96 that is formed into a generally hollow, cylindrical substrate 45, 85. Likewise, FIG. 14D illustrates a relatively thin sheet, layer or film of a finely woven wire mesh material 98 that is formed into a generally hollow, cylindrical substrate 45, 85. In each instance, the aerosol agent and the aerosol forming agent are applied to the material 92, 94, 96, 98 of the substrate 45, 85 in a suitable manner that facilitates vaporization of the aerosol agent from the substrate of the substrate holder. As previously mentioned hereinabove, the finely woven wire mesh material 98 may also, or alternatively, be utilized to form the thermally conductive heat sink 44 of the substrate holder 40, the heating element 68 of the heat generator 60, and/or the auxiliary heating element 74 of the auxiliary heat generator 70.

The aerosol agent delivery devices 10, 50 of the present invention are each designed to deliver a wide range of aerosol agents to a user, for example a therapeutic drug in the form of an aerosol to a patient for inhalation therapy, or nicotine in the form or an aerosol to a smoker. Regardless, the aerosol agent is provided to the user in an effective, yet convenient, portable and simple to use device for repeatedly and reliably vaporizing and delivering the aerosol agent. The aerosol agent delivered to the user consists essentially of air, the aerosol agent (e.g. therapeutic drug, nicotine, etc.) and the aerosol forming agent. The aerosol agent may also contain any desired flavorant or inert additive for improving the taste, consistency or texture of the aerosol agent, thereby making the inhalation therapy more palatable to a patient or to a smoker. The aerosol agent should have no significant mutagenic activity as measured by the industry standard Ames test. An aerosol agent delivery device 10 according to the present invention, when used properly, should deliver very low levels of carbon monoxide, preferably less than about 1 mg total CO delivery over the life of the device, more preferably less than about 0.5 mg total CO delivery, and most preferably essentially no total CO delivery.

The foregoing is a description of various embodiments of the invention that are given here by way of example only. Although aerosol agent delivery devices for vaporizing and delivering an aerosol agent to a user have been described herein with reference to the accompany drawing figures in which exemplary embodiments are shown, other embodiments of the invention may exist or become later known that perform similar functions and/or achieve similar results. All such equivalents are within the spirit and scope of the present invention, and thus, are intended to fall within the broadest reasonable interpretation of the appended claims consistent with this specification.

That which is claimed is:

1. A device for vaporizing and delivering an aerosol agent to a user, the device comprising:
    a heat generator operable for generating heat;
    a heat conductor configured to be in heat conducting relation with the heat generator, the heat conductor having an annular portion operable for conducting heat generated by the heat generator;
    a substrate holder configured to be received by the heat conductor in heat conducting relation with the annular portion of the heat conductor;
    a substrate disposed within the substrate holder and positioned concentrically relative to the annular portion of the heat conductor with the substrate holder received by the heat conductor, the substrate supporting an aerosol agent and an aerosol forming agent thereon, the aerosol forming agent operable for vaporizing the aerosol agent in response to heat generated by the heat generator and conducted to the substrate via the annular portion of the heat conductor, and the substrate holder operable for delivering the aerosol agent to the user in the form of an aerosol through the substrate holder.

2. The device according to claim 1, wherein the annular portion of the heat conductor defines an annular heat conducting chamber.

3. The device according to claim 2, wherein the annular heat conducting chamber of the heat conductor is defined by a relatively thin, double-walled housing.

4. The device according to claim 3, wherein the housing is made of a substantially rigid material selected from the group consisting of metal, hard plastic, glass, ceramic and the like.

5. The device according to claim 4, wherein the heat conductor defines a first recess for receiving the heat generator therein, a second recess for receiving an end of the substrate holder therein, and a third recess in fluid communication with the second recess and with the ambient atmosphere.

6. The device according to claim 1, wherein the heat generator is a handheld, portable torch comprising a heating element activated by a switch that utilizes a fuel source consisting essentially of a combustible liquefied gas.

7. The device according to claim 6, wherein the combustible liquefied gas is selected from the group comprising liquefied petroleum gas (LPG or LP-gas), propane, propylene, butylenes, butane, isobutene, methyl propane and n-butane.

8. The device according to claim 6, wherein the combustible liquefied gas is ignited by a piezo electronic igniter.

9. The device according to claim 1, wherein the substrate is made of a semi-porous material selected from the group consisting of cellulose-based material and expanded starch-based material adsorbed with an admixed solution of the aerosol agent and the aerosol forming agent.

10. The device according to claim 1, wherein the substrate comprises a finely woven wire mesh having the aerosol agent and the aerosol forming agent deposited thereon.

11. The device according to claim 1, wherein the aerosol forming agent is a polyol selected from the group consisting of glycerin, glycerol, propylene glycol, 1,3-butylene glycol, triethylene glycol, glycerol esters, propylene carbonate, and mixtures thereof.

12. The device according to claim 1, wherein the heat generator comprises a battery and a heating element electrically coupled to the battery, the heating element comprising a nichrome heating coil formed by an elongate length of a nichrome wire wound about the annular portion of the heat conductor, the substrate being positioned concentrically relative to the nichrome heating coil.

13. The device according to claim 12, wherein the heating element is activated by a switch electrically connected between the battery and at least one end of the elongate length of the nichrome wire.

14. The device according to claim 13, further comprising an auxiliary heat generator comprising an auxiliary heating element positioned adjacent the substrate disposed within the substrate holder and electrically connected to the battery through the switch.

15. The device according to claim 14, wherein the auxiliary heating element is formed by a finely woven wire mesh.

16. The device according to claim 1, wherein the substrate is made of at least one of a shredded cellulose-based material and an expanded starch-based material.

17. The device according to claim 1, wherein the substrate holder comprises an elongate, cylindrical, generally hollow aerosol delivery tube and an annular heat sink made of a thermally conductive material that is disposed between the heat conductor and the substrate and positioned concentrically relative to the annular portion of the heat conductor.

18. The device according to claim 1, wherein the substrate holder comprises an elongate, cylindrical, generally hollow aerosol delivery tube configured for containing the substrate at one end thereof, a filter portion at an opposite end thereof, and a filler portion disposed medially between the substrate and the filter portion, each of the aerosol delivery tube, substrate, filter portion and filler portion being made of a cellulose-based material.

19. The device according to claim 1, wherein the substrate holder comprises an elongate, annular aerosol delivery tube and wherein the substrate defines a central opening for drawing ambient air through the substrate and the aerosol delivery tube.

20. An aerosol agent delivery device comprising:
    a heat generator comprising a heating element operable for generating heat utilizing a fuel source consisting essentially of a combustible liquefied gas;
    a heat conductor in fluid communication with the heating element of the heat generator, the heat conductor having an annular portion defining an annular heat conducting chamber operable for conducting heat generated by the heating element;
    an elongate, cylindrical, generally hollow substrate holder configured to be received by the annular portion of the heat conductor and in heat conducting relation with the heating element of the heat generator via the annular portion of the heat conductor; and
    a substrate disposed within the substrate holder, the substrate holder being received by the heat conductor such that the substrate is positioned concentrically relative to the annular portion of the heat conductor, the substrate supporting an aerosol agent and an aerosol forming agent thereon, the aerosol forming agent being adapted for vaporizing the aerosol agent in response to heat generated by the heating element of the heat generator and conducted to the substrate via the annular portion of the heat conductor, and the substrate holder being adapted for delivering the aerosol agent to the user in the form of an aerosol when the aerosol forming agent vaporizes the aerosol agent supported on the substrate in response to the heat generated by the heating element of the heat generator and conducted to the substrate through the annular portion of the heat conductor.

21. The device according to claim 20, wherein the substrate holder comprises an elongate, annular aerosol delivery tube and wherein the substrate defines a central opening for drawing ambient air through the substrate and the aerosol delivery tube.

22. An aerosol agent delivery device comprising:
- a heat generator operable for generating heat, the heat generator comprising a battery, a heating element and a switch for electrically connecting the heating element to the battery;
- a heat conductor in heat conducting relation with the heat generator, the heat conductor having an annular receiver operable for conducting the heat generated by the heating element of the heat generator;
- an elongate, cylindrical, generally hollow substrate holder configured to be received by the annular receiver of the heat conductor in heat conducting relation with the heating element of the heat generator; and
- a substrate disposed within the substrate holder and positioned concentrically relative to the annular receiver of the heat conductor, the substrate supporting an aerosol agent and an aerosol forming agent thereon, the aerosol forming agent being adapted for vaporizing the aerosol agent in response to the heat generated by the heating element of the heat generator and conducted to the substrate via the annular receiver of the heat conductor, and the substrate holder being adapted for delivering the aerosol agent to the user in the form of an aerosol when the heating element of the heat generator heats the substrate through the annular receiver of the heat conductor and the substrate holder.

23. The device according to claim 22, wherein the substrate holder comprises an elongate, annular aerosol delivery tube and wherein the substrate defines a central opening for drawing ambient air through the substrate and the aerosol delivery tube.

24. An aerosol agent delivery device, comprising:
- a heat generator operable for generating heat and in heat conducting relation with an annular portion of a heat conductor; and
- a substrate holder in heat conducting relation with the annular portion of the heat conductor, the substrate holder comprising:
    - an annular aerosol delivery tube defining a longitudinally extending first central opening; and
    - an annular substrate disposed within the substrate holder and positioned concentrically relative to the annular portion of the heat conductor, the substrate being formed of a semi-porous material selected from the group consisting of a cellulose-based material, an expanded starch-based material, and a finely woven wire mesh material comprising an aerosol agent, the substrate defining a longitudinally extending second central opening in fluid communication with the first central opening of the aerosol delivery tube and with a source of ambient air to permit a user to draw the ambient air through the substrate and the aerosol delivery tube and thereby deliver the aerosol agent when the heat generated by the heat generator is conducted to the substrate via the annular portion of the heat conductor and the aerosol agent is vaporized.

* * * * *